United States Patent
Powell

(10) Patent No.: US 7,619,113 B2
(45) Date of Patent: Nov. 17, 2009

(54) METHOD AND APPARATUS FOR MAKING ACETIC ACID WITH IMPROVED PURIFICATION

(75) Inventor: Nathan Kirk Powell, Waxahachie, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 11/904,574

(22) Filed: Sep. 27, 2007

(65) Prior Publication Data
US 2009/0088587 A1  Apr. 2, 2009

(51) Int. Cl.
C07C 51/12 (2006.01)
C07C 53/08 (2006.01)

(52) U.S. Cl. ...................... 562/519; 562/607
(58) Field of Classification Search .......... None
See application file for complete search history.

(56) References Cited

U.S. PATENT DOCUMENTS

| | | | |
|---|---|---|---|
| 4,039,395 A | 8/1977 | Eby | 203/38 |
| 5,144,068 A | 9/1992 | Smith et al. | 562/519 |
| 5,877,347 A | 3/1999 | Ditzel et al. | 562/519 |
| 5,877,348 A | 3/1999 | Ditzel et al. | 562/519 |
| 5,883,295 A | 3/1999 | Sunley et al. | 562/519 |
| 6,114,576 A | 9/2000 | Leet et al. | 562/519 |
| 6,458,996 B1 | 10/2002 | Muskett | 562/536 |
| 6,642,413 B2 | 11/2003 | Thiebaut | 562/517 |
| 7,345,197 B1* | 3/2008 | Hallinan et al. | 562/519 |
| 2003/0144548 A1 | 7/2003 | Huckman et al. | 562/519 |
| 2005/0197508 A1 | 9/2005 | Scates et al. | 562/608 |
| 2006/0247466 A1 | 11/2006 | Zinobile et al. | 562/517 |
| 2008/0051601 A1* | 2/2008 | Sawyer et al. | 562/550 |

OTHER PUBLICATIONS

Applied Homogeneous Catalyst With Organometallic Compounds, Cornils et al., Ed. (Beach Edition) (Wylie, Weinheim, Federal Republic of Germany 2000), Chapter 2, Parts 2.1.2 and following, pp. 104-137.

* cited by examiner

Primary Examiner—Karl J Puttlitz

(57) ABSTRACT

An improved method of producing acetic acid includes condensing overhead vapor from a light ends column and decanting the condensed vapor to a light phase and a heavy phase. The heavy phase consists predominantly of methyl iodide and at least a portion of the decanted heavy phase is refluxed to the light ends column. Acetic acid content of the light ends column overhead stream and water content of the light ends column product (sidedraw) stream are both decreased, improving purification efficiency.

17 Claims, 3 Drawing Sheets

METHOD AND APPARATUS FOR MAKING ACETIC ACID WITH IMPROVED PURIFICATION

TECHNICAL FIELD

The present invention relates generally to an apparatus and method for producing acetic acid wherein reflux to the light ends column is from a heavy organic phase derived from the column overhead. Acetic acid content of the product stream is increased, while water content is reduced.

BACKGROUND ART

Carbonylation processes are well known in the art. Of particular commercial significance are processes for the carbonylation of methanol to make acetic acid and processes for the carbonylation of methyl acetate to make acetic anhydride. See Applied Homogeneous Catalyst With Organometallic Compounds, Cornils et al., Ed. (Bench Edition) (Wylie, Weinheim, Federal Republic of Germany 2000), Chapter 2, Parts 2.1.2 and following, pp. 104-137. See, also, U.S. Pat. No. 6,458,996 to Muskett; U.S. Pat. No. 6,642,413 to Thiebaut, as well as U.S. Pat. No. 6,114,576 to Leet et al.; U.S. Pat. No. 4,039,395 to Eby; and U.S. patent application Ser. No. 11/116,771 (Pub. No. US2006/0247466) of Zinoble et al.; Ser. No. 10/708,420 (Publication No. US2005/0197508) of Scates et al. and Ser. No. 10/058,547 (Publication No. US2003/0144548) of Huckman et al.

To make acetic acid, one method of choice involves carbonylating methanol in a homogeneous reaction medium wherein rhodium is utilized as a catalyst. Generally, the reaction medium includes catalyst, water, acetic acid, dissolved carbon monoxide (CO), methanol, methyl acetate (MeAc), hydriodic acid (HI), methyl iodide and optionally one or more promoters and/or stabilizers. Methanol and carbon monoxide are fed to a reactor as feedstocks. A portion of the reaction medium is continuously withdrawn and provided to a flasher where product is flashed off and sent (as vapor) to a purification train. The purification train includes a light ends column which removes "light" or low boiling components as overhead and provides a product stream for further purification. A particularly preferred carbonylation process is taught in U.S. Pat. No. 5,144,068 to Smith et al. In this so called "low water" process, an alcohol such as methanol is reacted with carbon monoxide in a liquid reaction medium containing a rhodium catalyst stabilized with an iodide salt, especially lithium iodide along with methyl iodide and methyl acetate in specified proportions. With a finite concentration of water in the reaction medium, the product is the carboxylic acid instead of, for example, the anhydride. The reaction system of the '068 patent not only provides an acid product of unusually low water content at unexpectedly favorable rates, but also exhibits unexpectedly high catalyst stability. That is, the catalyst is resistant to catalyst precipitation out of the reaction medium.

Another method of choice for carbonylating methanol involves utilizing a homogeneous iridium catalyst in the reactor. There is disclosed, for example, in U.S. Pat. No. 5,883,295, to Sunley et al. a process for the production of acetic acid comprising carbonylating with carbon monoxide methanol and/or a reactive derivative thereof, in the substantial absence of a metal promoter and/or ionic iodide co-promoter in a carbonylation reactor containing a liquid reaction composition with an iridium carbonylation catalyst, methyl iodide co-catalyst, water, acetic acid, and methyl acetate wherein there is maintained in the liquid reaction composition: (a) water at a concentration of less than 5% by weight; (b) methyl iodide in a concentration of greater than 12% by weight and (c) in the carbonylation reactor a total pressure of less than 50 bar. See, also, U.S. Pat. No. 5,877,348 to Ditzel et al. and U.S. Pat. No. 5,877,347 also to Ditzel et al.

Frequent production limitations in the purification section of an acetic acid unit are the light ends column and the dehydrating column. The light ends column receives a hot vapor product stream from the flasher and operates to remove most of the methyl acetate (MeAc) and methyl iodide (MeI) from the stream before the product stream is fed forward for water removal to the dehydration column.

In a typical acetic acid methanol carbonylation process, hot high pressure liquid from the reactor is reduced in pressure across a valve and flashed in a lower pressure flasher vessel. The vapors liberated from this step are fed near the bottom of a light ends (LE) tower. Condensed liquids rich in acetic acid are removed from a liquid sidedraw above the feed and fed forward for further purification, while vapors exiting the tower overhead are condensed and fed to a liquid-liquid decanter (LE OH decanter). Conventionally, the light phase from the LE OH decanter is refluxed to the LE tower and the heavy phase is recycled to the reactor feed. Total reflux of the light phase in the LE tower forces a higher concentration of water into the LE tower product sidedraw because of a partial condensation of the feed. This higher sidedraw water content requires high reflux rates in the drying column and results in higher dehydration tower loading. Recycle of the light phase to the reactor will reduce water content in the sidedraw, but the concentration of acetic acid in the light phase from the LE tower decanter may be 15% or more and gets higher as the light phase is recycled. The restrictive vapor-liquid equilibrium (VLE) between acetic acid and water forces significant quantities of acetic acid into the LE column overhead product. As the light phase is recycled, the light phase reflux rate decreases and the problem gets worse.

SUMMARY OF INVENTION

In accordance with the present invention, the heavy phase instead of the light phase from the LE OH decanter is refluxed in the LE column. The heavy phase from the LE OH decanter is predominantly methyl iodide, which has much more favorable VLE with acetic acid than water. As a result, vapors contacted with heavy phase reflux are much more efficiently reduced in acetic acid concentration (from, for example, 7% or more to less than 1%). The light phase acetic acid content is reduced so that it can be recycled directly to the reactor without a loss of reflux rate. Heavy phase distillate is also recycled to the reactor, at a rate to keep the liquid sidedraw adequately low in MeI and MeAc and to control the acetic acid profile in the LE tower. This can be accomplished by manipulating the reflux rate to maintain a temperature breakpoint somewhere in the middle of the tower.

The reduced water content in the liquid sidedraw of the LE tower relieves VLE restrictions in the drying column and allows a reduction in dehydration column reflux rate. In addition, the lower acid content in the LE OH decanter results in a light phase stream lower in both acetic acid and methyl iodide concentration, potentially aiding in aldehyde removal. If higher capacities are desired, the reduced reflux rate on the dehydration column will allow approximately 15% higher rates to the drying column.

BRIEF DESCRIPTION OF DRAWINGS

The invention is described in detail below with reference to the following drawings wherein like numerals designate similar parts and wherein.

DESCRIPTION OF THE PREFERRED EMBODIMENTS

Figure 1:
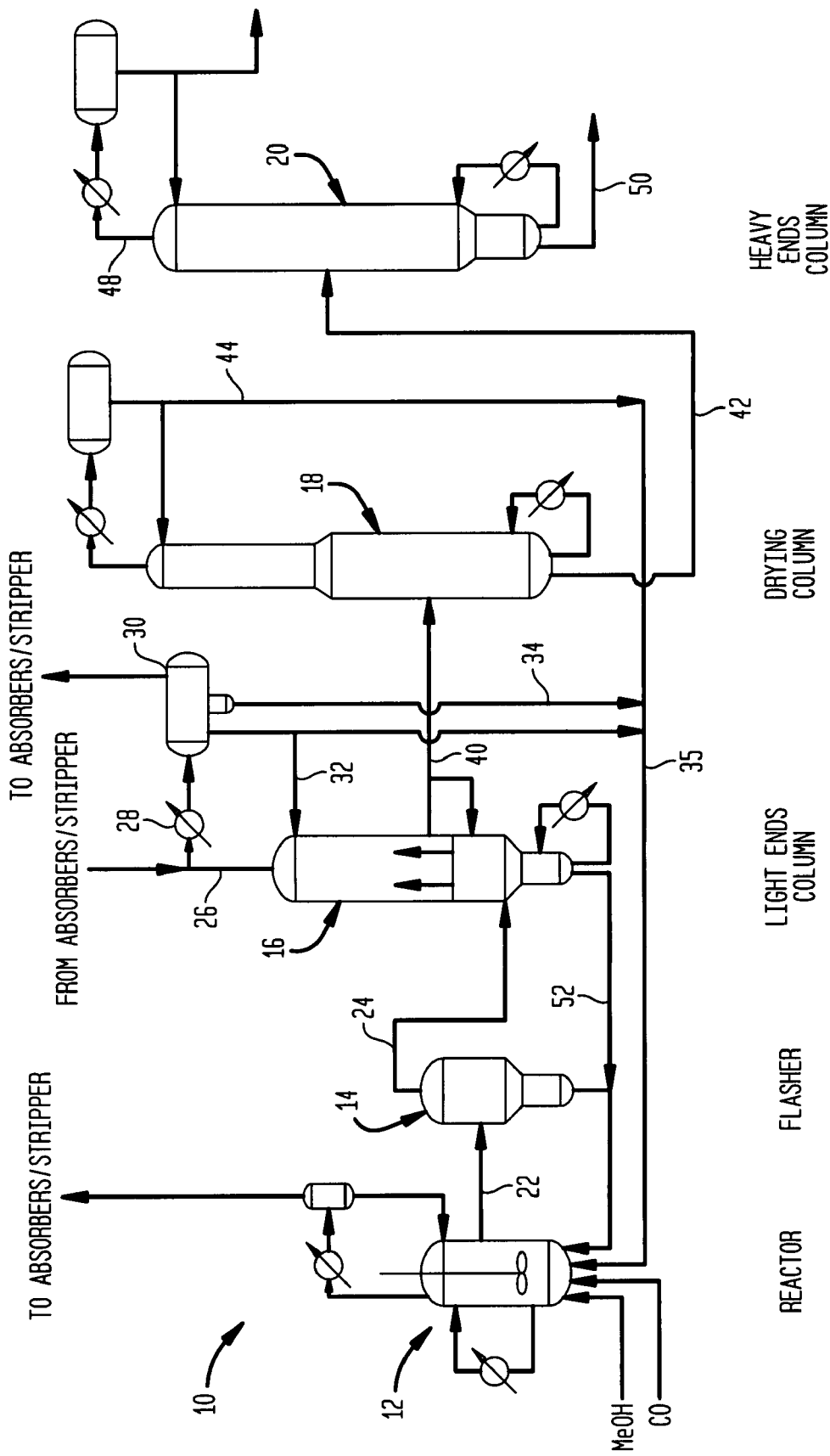
FIG. 1 is a schematic diagram of a conventional methanol carbonylation unit.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. %, ppb and like terms refer to weight percent, parts per billion by weight and so forth, unless otherwise indicated.

"Predominantly" means more than 50% by weight. Predominantly acetic acid and water, for example, means that acetic acid and water collectively make up more than 50% by weight of a composition.

The Group VIII catalyst may be a rhodium and/or iridium catalyst. The rhodium metal catalyst may be added in any suitable form such that rhodium is in the catalyst solution as an equilibrium mixture including $[Rh(CO)_2I_2]^-$ anion as is well known in the art. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. No. 5,001,259 to Smith et al.; U.S. Pat. No. 5,026,908 to Smith et al.; and U.S. Pat. No. 5,144,068, also to Smith et al., the disclosures of which are hereby incorporated by reference.

Similarly, an iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

An alkyl halide co-catalyst/promoter is generally used in combination with the Group VIII metal catalyst component. Methyl iodide is a preferred as the alkyl halide promoter. Preferably, the concentration of alkyl halide in the liquid reaction composition is in the range 1 to 50% by weight, preferably 2 to 30% by weight.

The alkyl halide promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbonylation apparatus or process that is the subject of the invention includes generally at least a reactive section, and a purification section. The present invention may be appreciated in connection with, for example, the carbonylation of methanol with carbon monoxide in a homogeneous catalytic reaction system comprising a reaction solvent (typically acetic acid), methanol and/or its reactive derivatives, a soluble rhodium catalyst, at least a finite concentration of water, optionally including an iodide salt. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range 0.1 to 16% by weight, more preferably 1 to 14% by weight, most preferably 1 to 10% by weight.

The reaction liquid is typically drawn from the reactor and flashed. The crude vapor product stream from the flasher is sent to a purification system which generally includes at least a light ends column and a dehydration column. Carbonylation system may use only 2 purification columns and is preferably operated as described in more detail in U.S. Pat. No. 6,657,078 to Scates et al., entitled "Low Energy Carbonylation Process", the disclosure of which is incorporated herein by reference.

Figure 2:
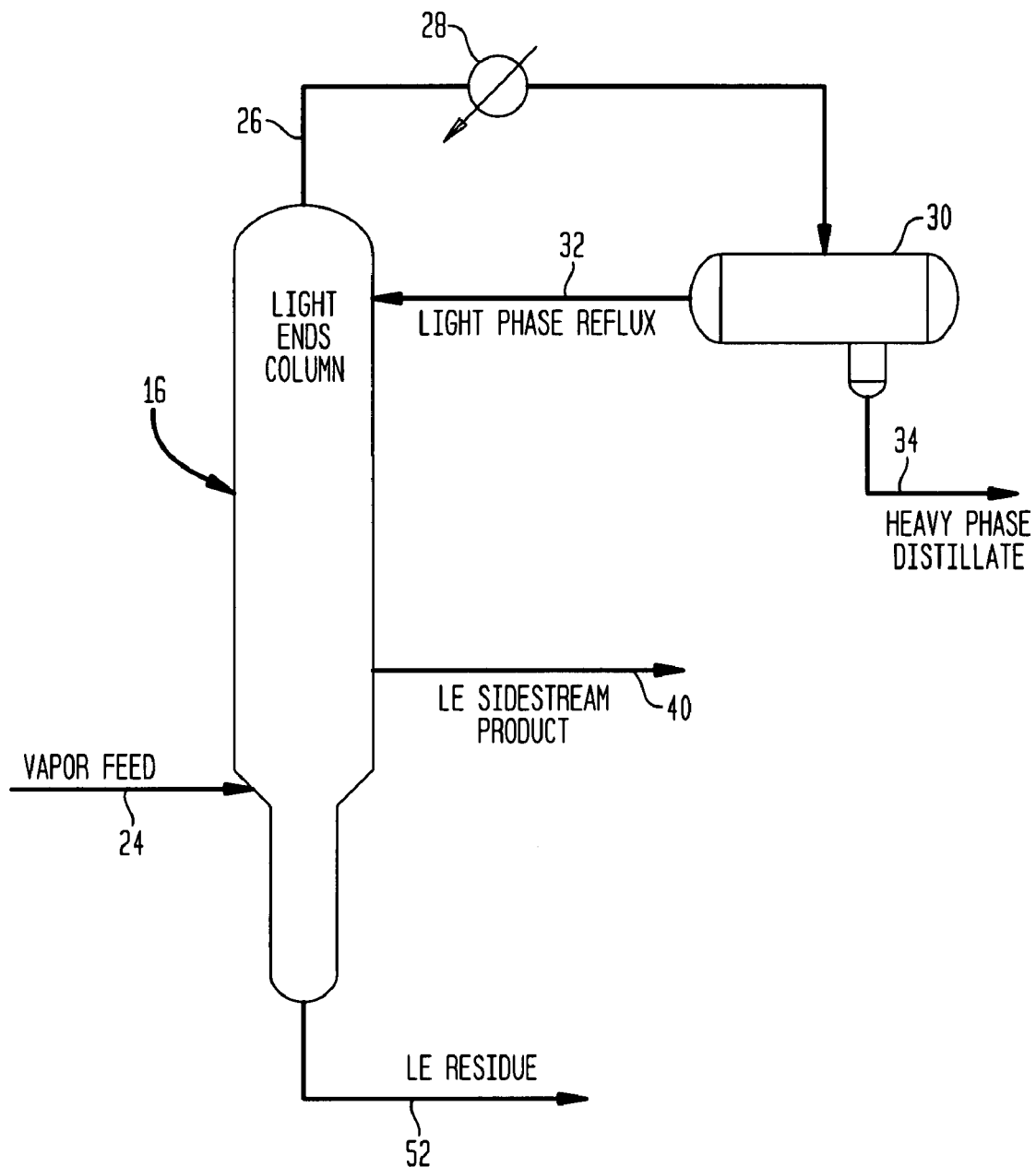
FIG. 2 is a detail of the apparatus of FIG. 1 illustrating reflux from decanter 30 of a light decanted phase.
Figure 3:
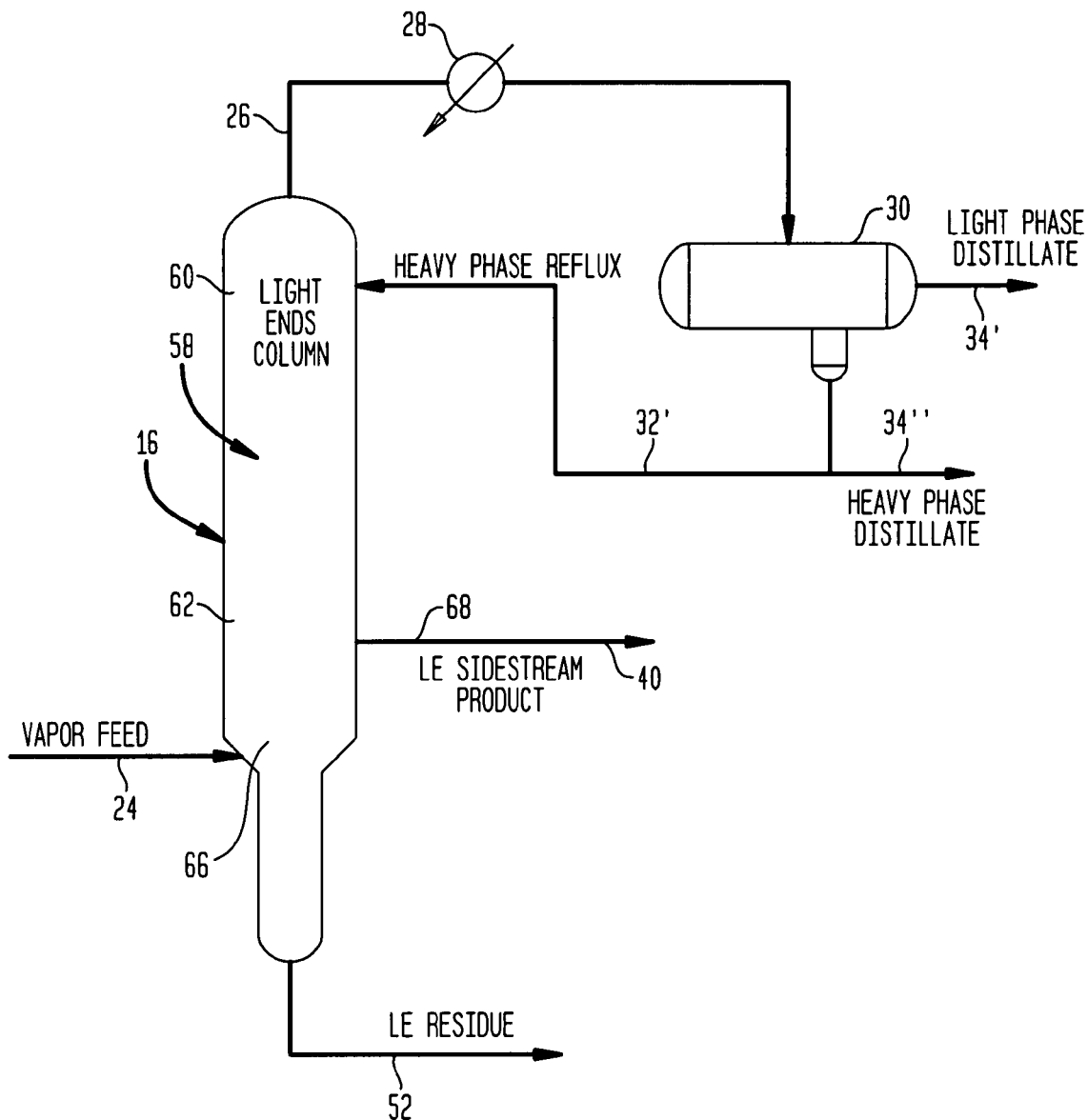
FIG. 3 is a detail of the apparatus of FIG. 1 illustrating reflux from decanter 30 of a heavy decanted phase.

Referring to FIGS. 1 through 3, there is shown a carbonylation unit 10 of the class utilized in connection with the present invention. Unit 10 includes a reactor 12, a flasher 14, a light ends column 16, a drying or dehydration column 18 as well as heavy ends column 20. Reactor 12 includes the reaction medium and there is fed thereto methanol and carbon monoxide. A portion of the reaction medium is continuously provided to flasher 14 via line 22 where crude product is flashed and sent to light ends column 16 via line 24 as a hot vapor feed.

A gaseous purge stream is typically vented from the head of the reactor to prevent buildup of gaseous by-products such as methane, carbon dioxide and hydrogen and to maintain a set carbon monoxide partial pressure at a given total reactor pressure. Optionally (as illustrated in Chinese Patent No. ZL92108244.4), a so-called "converter" reactor can be employed which is located between the reactor and flash vessel 14 shown in FIG. 1. The "converter" produces a vent stream comprising gaseous components which are typically scrubbed with a compatible solvent to recover components such as methyl iodide and methyl acetate. The gaseous purge streams from the reactor and converter can be combined or scrubbed separately and are typically scrubbed with either acetic acid, methanol or mixtures of acetic acid and methanol to prevent loss of low boiling components such as methyl iodide from the process. If methanol is used as the vent scrub liquid solvent, the enriched methanol from the scrubbing system is typically returned to the process by combining with the fresh methanol feeding the carbonylation reactor—although it can also be returned into any of the streams that recycle back to the reactor such as the flasher residue or light ends or dehydration column overhead streams. If acetic acid is used as the vent scrub liquid solvent, the enriched acetic acid from the scrubbing system is typically stripped of absorbed light ends and the resulting lean acetic acid is recycled back to the absorbing step. The light end components stripped from the enriched acetic acid scrubbing solvent can be returned to the main process directly or indirectly in several different locations including the reactor, flasher, or purification columns. Optionally, the gaseous purge streams may be vented through the flasher base liquid or lower part of the light ends column to enhance rhodium stability and/or they may be combined with other gaseous process vents (such as the purification column overhead receiver vents) prior to scrubbing. These variations are well within the scope of the present invention as will be appreciated from the appended claims and the description which follows.

In column 16, the product is purified of light components which exit the column via line 26, are condensed in a first condenser 28 and then decanted in a decanter 30. Conventionally, the light phase from decanter 30 is refluxed to column 16 via line 32, while the heavy phase from decanter 30 is returned to the reactor via lines 34, 35. Also provided, but not shown, are absorbers and strippers used to recycle material into the system.

A purified product stream 40 is withdrawn as a (preferably liquid) sidestream from column 16 and fed to drying column 18 where water is removed from the partially purified product. Thereafter, the dried product is provided to heavy ends column 20 via line 42, while the overhead and some product acetic acid is used as reflux for column 18 or recycled to the reactor via lines 34, 44. Product acetic acid is taken overhead from heavy ends column 20 via line 48, while heavy waste is removed via line 50.

Column 16 generates a liquid residue stream 52 which is conventionally recycled with flasher residue to the reactor as shown.

Referring specifically to FIG. 3, there is shown a light ends column 16 configured in accordance with the present invention. Column 16 is coupled to flasher 12 (FIG. 1) via line 24. Column 16 defines a distillation zone 58 with an upper portion 60, a central portion 62, and a lower portion 66. A liquid sidedraw 68 provides an outlet for product stream 40 as shown. Distilled overhead vapor exits column 16 through line 26 where it is fed to condenser 28. In condenser 28, vapor is condensed and fed as liquid to decanter 30. In decanter 30, the condensed vapor is decanted into a light phase distillate as well as a heavy phase distillate which consists predominantly of methyl iodide. Light phase distillate, on the other hand, consists predominantly of water and acetic acid. In accordance with the present invention the acetic acid content of light phase distillate is substantially reduced so that the light phase may be recycled to reactor 12 via line 34' if so desired. All or a portion of the heavy phase is drawn from decanter 30 by way of line 32' and fed as reflux to column 16 at upper portion 60 of distillation zone 58 as reflux. A fraction of the heavy phase distillate is recycled to the reactor via line 34" along with the light phase distillate. Stream 40 is fed from sidedraw 68 to drying column 18 as is shown in FIG. 1.

Operation of the systems of FIGS. 1, 2 and 3 was simulated with an empirical computer model to illustrate the effects of recycling heavy phase material from decanter 30 instead of light phase material.

Relative values of various mass flow in the system with light phase reflux versus heavy phase reflux are given in Table 1 along with calculated acetic acid content values. By "relative mass flow" we refer to the calculated mass flow in a particular point in the system relative to a base case where the system of FIGS. 1 and 2 is operated with a total light phase reflux from decanter 30. Thus a relative mass flow in pounds per hour crude product stream to the light ends column of 1 indicates that both systems were operated at the same feed rate (and composition in this simulation) to the light ends column. The relative mass flow rate of light ends product side stream was substantially the same. The relative mass reflux in the light ends column was substantially higher when using heavy phase reflux, otherwise conditions were pretty much identical.

TABLE 1

Comparison of LE Column Operation With Light Phase Reflux Versus Heavy Phase Reflux

|  | With Light Phase Reflux | With Heavy Phase Reflux |
|---|---|---|
| Relative Mass Flow lbs/hour of Crude Product Stream to LE Column | 1 | 1 |
| Relative Mass Flow lbs/hour of LE Product Sidestream | 1 | 1 |
| Relative Reflux in LE Column (Mass) | 1 | 3.5 |
| Acetic Acid Content of OH (%) | >5% | <0.5% |
| Approximate Acetic Acid Concentration in LE Product Sidestream | 93% | 94% |
| Relative Mass Flow Rate of Water in LE Product Sidestream | 1 | 0.55 |
| Acetic Acid Concentration in Decanted Light Phase | >10 | <2 |

It is seen in Table 1 that when operated under substantially identical conditions with identical feed, the system using heavy phase reflux had a much lower concentration of acetic acid in the overhead vapor of the light ends column as compared with a substantially identical system operated with light phase reflux. Likewise, the relative mass flow rate of water in the light ends product sidestream was significantly lower when using heavy phase reflux even though the relative mass flow rate of the product side stream was the same. Moreover, acetic acid concentration in the decanted light phase is much lower when the system is operated with heavy phase reflux; while the LE product sidestream had a higher acetic acid concentration.

Thus, the inventive system includes purifying a crude product stream in an acetic acid carbonylation process which includes: i) condensing overhead vapor from the distillation zone of a light ends column; ii) decanting the condensed vapor into a heavy phase comprising predominantly methyl iodide and a light phase comprising predominantly acetic acid and water; and iii) refluxing at least a portion of the heavy phase to the distillation zone of the light ends column. The purified product stream in the light ends column is fed forward to a drying column for further purification.

Generally, anywhere from about 40% to about 90% by weight of the condensed heavy phase from decanter 30 is refluxed to the distillation zone of the light ends column. At least about 50%, at least about 60% or at least about 70% by weight or more of the decanted heavy phase may be refluxed. So also, the overhead vapor in accordance with the inventive method of operation has an acetic acid content of less than about 5%; usually less than 2.5%; and most typically less than 1% by weight based on the total weight of vapor exiting column 16. The decanted heavy phase typically has a methyl iodide content between about 60% by weight and 90% by weight.

It is seen from the foregoing simulation that the purified product stream has a relative water content from about 0.4 times to about 0.85 times that of a product stream drawn from a substantially identical light ends column operated under substantially identical conditions refluxing the decanted light phase instead of the decanted heavy phase. Typically the purified product stream of the inventive process has a relative water content of about 0.75 times or 0.6 times or less than that of a product stream drawn from a substantially identical light ends column operated under substantially identical conditions refluxing the decanted light phase instead of the decanted heavy phase.

The decanted light phase may have an acetic acid content of less than 5% by weight, less than 2% by weight or less than 1% by weight. A particularly preferred process of the invention uses a so-called "low water" reaction mixture. In this process the step of carbonylating methanol includes: reacting methanol with a carbon monoxide feedstock in a carbonylation reactor holding a catalytic reaction mixture while maintaining in the reaction mixture during the course of the reaction at least a finite concentration of from about 0.1 weight percent up to less than 14 weight percent of water together with (i) a salt soluble in the reaction mixture at the reaction temperature in an amount operative to maintain a concentration of ionic iodide in the range of from about 2 to about 20 weight percent effective as a catalyst stabilizer and co-promoter, (ii) from about 1 to 20 weight percent methyl iodide, (iii) from about 0.5 to about 30 weight percent methyl acetate, (iv) a rhodium catalyst, and (v) acetic acid.

The invention has been described in detail and illustrated in connection with numerous embodiments. Modifications to specific embodiments within the spirit and scope of the present invention will be readily apparent to those of skill in the art. Such modifications are within the spirit and scope of the present invention which is set forth in the appended claims.

What is claimed is:

1. A carbonylation process for producing acetic acid comprising:
   (a) carbonylating methanol or its reactive derivatives in the presence of water, a catalyst selected from rhodium catalysts, iridium catalysts and mixtures thereof, and a methyl iodide promoter to form an acetic acid reaction mixture in a reactor;
   (b) separating the stream of the acetic acid reaction mixture into a liquid recycle stream and a crude product stream including acetic acid, methyl iodide, methyl acetate and water;
   (c) feeding the crude product stream to a light ends column having a distillation zone;
   (d) purifying the crude product stream in the distillation zone of the light ends column to remove methyl iodide and methyl acetate and generate a purified product stream, the purified product stream having a lower concentration of methyl iodide and methyl acetate than the crude product stream, and wherein the step of purifying the crude product stream includes (i) condensing overhead vapor from the distillation zone of the light ends column, (ii) decanting the condensed vapor into a heavy phase comprising predominantly methyl iodide and a light phase comprising predominantly acetic acid and water, and (iii) refluxing at least a portion of the condensed heavy phase to the distillation zone of the light ends column; and
   (e) drawing a purified product stream from the light ends column.

2. The process according to claim 1, wherein from about 40% by weight to about 90% by weight of the condensed heavy phase is refluxed to the distillation zone of the light ends column.

3. The process according to claim 1, wherein at least about 50% by weight of the decanted heavy phase is refluxed to the distillation zone of the light ends column.

4. The process according to claim 1, wherein at least about 60% by weight of the decanted heavy phase is refluxed to the distillation zone of the light ends column.

5. The process according to claim 1, wherein at least about 70% by weight of the decanted heavy phase is refluxed to the distillation zone of the light ends column.

6. The process according to claim 1, wherein the overhead vapor has an acetic acid content of less than 5%.

7. The process according to claim 1, wherein the overhead vapor has an acetic acid content of less than 2.5%.

8. The process according to claim 1, wherein the overhead vapor has an acetic acid content of less than 1%.

9. The process according to claim 1, wherein the decanted heavy phase has a methyl iodide content between about 60% by weight and about 90% by weight.

10. The process according to claim 1, wherein the purified product stream has a relative water content of from about 0.4 times to about 0.85 times that of a product stream drawn from a comparative process, wherein the comparative process product stream is operated using a substantially identical light ends column refluxing the decanted light phase instead of the decanted heavy phase, and wherein the mass flow rate of the product side stream is essentially the same for both the process and the comparative process.

11. The process according to claim 1, wherein the purified product stream has a relative water content of 0.75 times or less than that of a product stream drawn from a substantially identical light ends column operated under substantially identical conditions refluxing the decanted light phase instead of the decanted heavy phase.

12. The process according to claim 1, wherein the purified product stream has a relative water content of 0.6 times or less than that of a product stream drawn from a substantially identical light ends column operated under substantially identical conditions refixing the decanted light phase instead of the decanted heavy phase.

13. The process according to claim 1, wherein the decanted light phase has an acetic acid content of less than 5% by weight.

14. The process according to claim 1, wherein the decanted light phase has an acetic acid content of less than 2% by weight.

15. The process according to claim 1, wherein the decanted light phase has an acetic acid content of less than 1% by weight.

16. The method according to claim 1, further comprising feeding the purified product stream forward for further purification, including water removal.

17. A carbonylation process for producing acetic acid comprising:
- (a) reacting methanol with a carbon monoxide feedstock in a carbonylation reactor holding a catalytic reaction mixture while maintaining in said reaction mixture during the course of said reaction at least a finite concentration of from about 0.1 weight percent up to less than 14 weight percent of water together with (i) a salt soluble in the reaction mixture at the reaction temperature in an amount operative to maintain a concentration of ionic iodide in the range of from about 2 to about 20 weight percent effective as a catalyst stabilizer and co-promoter, (ii) from about 1 to 20 weight percent methyl iodide, (iii) from about 0.5 to about 30 weight percent methyl acetate, (iv) a rhodium catalyst, and (v) acetic acid;
- (b) separating the stream of the acetic acid reaction mixture into a liquid recycle stream and a crude product stream including acetic acid, methyl iodide, methyl acetate and water;
- (c) feeding the crude product stream to a light ends column having a distillation zone;
- (d) purifying the crude product stream in the distillation zone of the light ends column to remove methyl iodide and methyl acetate and generate a purified product stream, the purified product stream having a lower concentration of methyl iodide and methyl acetate than the crude product stream, and wherein the step of purifying the crude product stream includes (i) condensing overhead vapor from the distillation zone of the light ends column, (ii) decanting the condensed vapor into a heavy phase comprising predominantly methyl iodide and a light phase comprising predominantly acetic acid and water, and (iii) refluxing at least a portion of the condensed heavy phase to the distillation zone of the light ends column; and
- (e) drawing a purified product stream from the light ends column.

* * * * *